(12) United States Patent
Alyami

(10) Patent No.: US 9,877,803 B2
(45) Date of Patent: Jan. 30, 2018

(54) ORTHODONTIC DEVICE

(71) Applicant: Dalma Medical Center, Najran (SA)

(72) Inventor: Bandar Alyami, Najran (SA)

(*) Notice: Subject to any disclaimer, the term of this patent is extended or adjusted under 35 U.S.C. 154(b) by 0 days.

(21) Appl. No.: 15/147,369

(22) Filed: May 5, 2016

(65) Prior Publication Data

US 2016/0354180 A1 Dec. 8, 2016

Related U.S. Application Data

(62) Division of application No. 13/961,652, filed on Aug. 7, 2013, now Pat. No. 9,333,053.

(51) Int. Cl.
*A61C 3/00* (2006.01)
*A61C 7/00* (2006.01)
*A61C 7/10* (2006.01)
*A61C 7/06* (2006.01)
*A61B 17/66* (2006.01)
*A61B 17/34* (2006.01)
(Continued)

(52) U.S. Cl.
CPC .......... *A61C 7/002* (2013.01); *A61B 17/3472* (2013.01); *A61B 17/663* (2013.01); *A61B 17/8071* (2013.01); *A61B 34/35* (2016.02); *A61C 7/06* (2013.01); *A61C 7/10* (2013.01); *A61C 7/145* (2013.01); *A61C 8/0096* (2013.01); *A61K 9/06* (2013.01); *A61K 35/32* (2013.01); *A61K 45/06* (2013.01); *A61K 47/36* (2013.01); *A61B 2017/00221* (2013.01)

(58) Field of Classification Search
CPC .... A61C 7/06; A61C 7/10; A61C 7/00; A61C 7/02; A61B 17/007; A61B 17/176; A61B 17/8866; A61B 17/8071

USPC ................................................... 433/6–9, 18
See application file for complete search history.

(56) References Cited

U.S. PATENT DOCUMENTS 3,391,693 A 7/1968 Georgiade et al.
3,977,082 A * 8/1976 Siatkowski .............. A61C 7/10
433/7

(Continued)

FOREIGN PATENT DOCUMENTS

DE 10234376 A1 * 2/2004 ............... A61C 7/10
EP 1 871 276 5/2012
(Continued)

OTHER PUBLICATIONS

B. R. Goldwaser, et al. "Continuous Mandibular Distraction Osteogenesis: Novel Device and Preliminary Results in Minipigs". America Association of Oral and Maxillofacial Surgeons, pp. 168-177. (2013).

(Continued)

*Primary Examiner* — Cris L Rodriguez
*Assistant Examiner* — Matthew Saunders
(74) *Attorney, Agent, or Firm* — Oblon, McClelland, Maier & Neustadt, L.L.P.

(57) ABSTRACT

An orthodontic/orthognathic device for correcting and changing tooth placements and bone structure, and a method of using orthodontic/orthognathic device for tooth movement, correcting syndromic conditions of the mouth and osteogenetic correction. The device may be used for maxillary distraction and expansion as well as mandibular separation and expansion. The device can be controlled by computer to direct tooth and bone placement.

12 Claims, 15 Drawing Sheets

(51) Int. Cl.
*A61K 9/06* (2006.01)
*A61K 35/32* (2015.01)
*A61K 45/06* (2006.01)
*A61K 47/36* (2006.01)
*A61B 34/35* (2016.01)
*A61B 17/80* (2006.01)
*A61C 7/14* (2006.01)
*A61C 8/00* (2006.01)
*A61B 17/00* (2006.01)

(56) References Cited

U.S. PATENT DOCUMENTS

| | | | |
|---|---|---|---|
| 4,482,318 A * | 11/1984 | Forster | A61C 7/10 433/7 |
| 5,066,224 A * | 11/1991 | Block | A61B 17/663 433/18 |
| 5,147,358 A | 9/1992 | Remmler | |
| 5,156,605 A | 10/1992 | Pursley | |
| 5,334,202 A | 8/1994 | Carter | |
| 5,540,687 A | 7/1996 | Fairley et al. | |
| 5,820,369 A * | 10/1998 | Kvarnstrom | A61B 17/663 433/173 |
| 5,829,970 A | 11/1998 | Yousefian | |
| 5,885,283 A | 3/1999 | Gittleman | |
| 5,902,304 A | 5/1999 | Walker et al. | |
| 6,547,796 B1 | 4/2003 | Chin | |
| 7,887,324 B2 | 2/2011 | Singh | |
| 8,057,472 B2 | 11/2011 | Walker et al. | |
| 8,177,789 B2 | 5/2012 | Magill et al. | |
| 8,348,665 B2 | 1/2013 | Kuo | |
| 8,662,889 B2 | 3/2014 | Baker | |
| 8,690,890 B2 | 4/2014 | Navas et al. | |
| 2003/0091952 A1 * | 5/2003 | Bowman | A61C 7/00 433/18 |
| 2003/0138755 A1 | 7/2003 | Tremont | |
| 2004/0199094 A1 | 10/2004 | Greene et al. | |
| 2005/0234448 A1 | 10/2005 | McCarthy | |
| 2005/0251136 A1 | 11/2005 | Noon et al. | |
| 2005/0260534 A1 * | 11/2005 | Belfor | A61C 7/10 433/24 |
| 2006/0184168 A1 | 8/2006 | Posnick | |
| 2006/0257811 A1 * | 11/2006 | Ohki | A61C 7/10 433/18 |
| 2007/0264605 A1 * | 11/2007 | Belfor | A61C 7/00 433/6 |
| 2008/0020339 A1 * | 1/2008 | Papadopoulos | A61C 7/00 433/21 |
| 2008/0051779 A1 | 2/2008 | Mackenzie | |
| 2008/0227046 A1 | 9/2008 | Lowe et al. | |
| 2008/0234554 A1 | 9/2008 | Vvedensky | |
| 2009/0087810 A1 * | 4/2009 | Singh | A61C 7/10 433/24 |
| 2009/0148804 A1 | 6/2009 | Marcus | |
| 2009/0192514 A1 * | 7/2009 | Feinberg | A61B 17/8004 606/90 |
| 2013/0310880 A1 | 11/2013 | Ruiz | |

FOREIGN PATENT DOCUMENTS

| | | |
|---|---|---|
| WO | 2008/032310 | 3/2008 |
| WO | 2011/155989 | 12/2011 |

OTHER PUBLICATIONS

M. D. Chung, et al. "An Implantable Battery System for Continuous Automatic Distraction Device for Mandibular Distraction Osteogenesis". Journal of Medical Devices, vol. 4., pp. 045005-1-045005-6. (Dec. 2010).

* cited by examiner

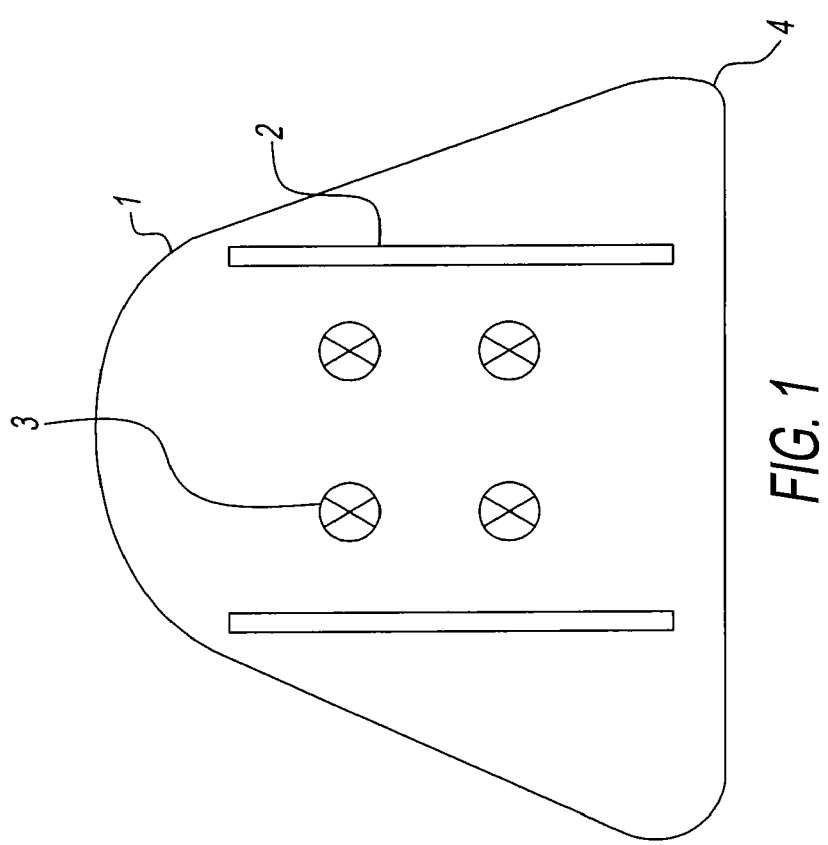

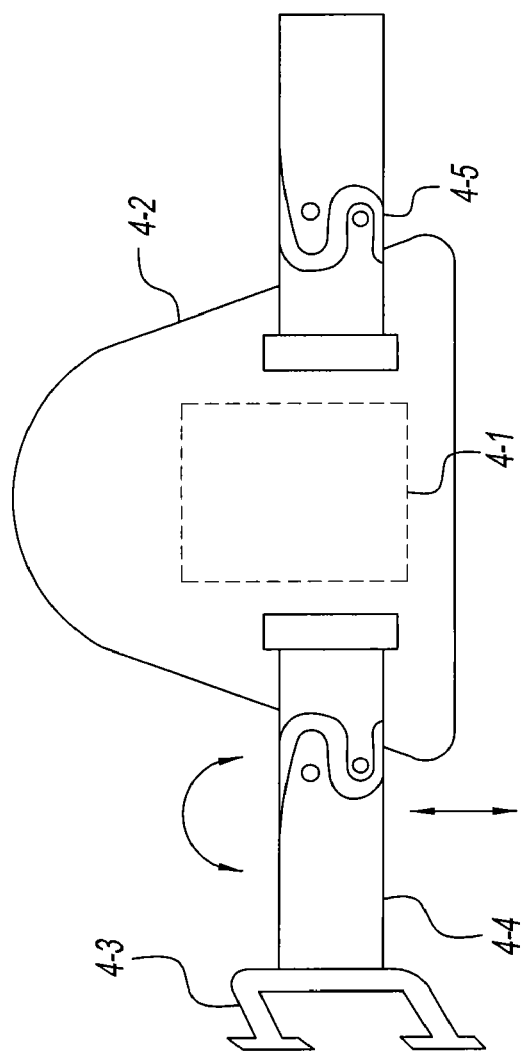

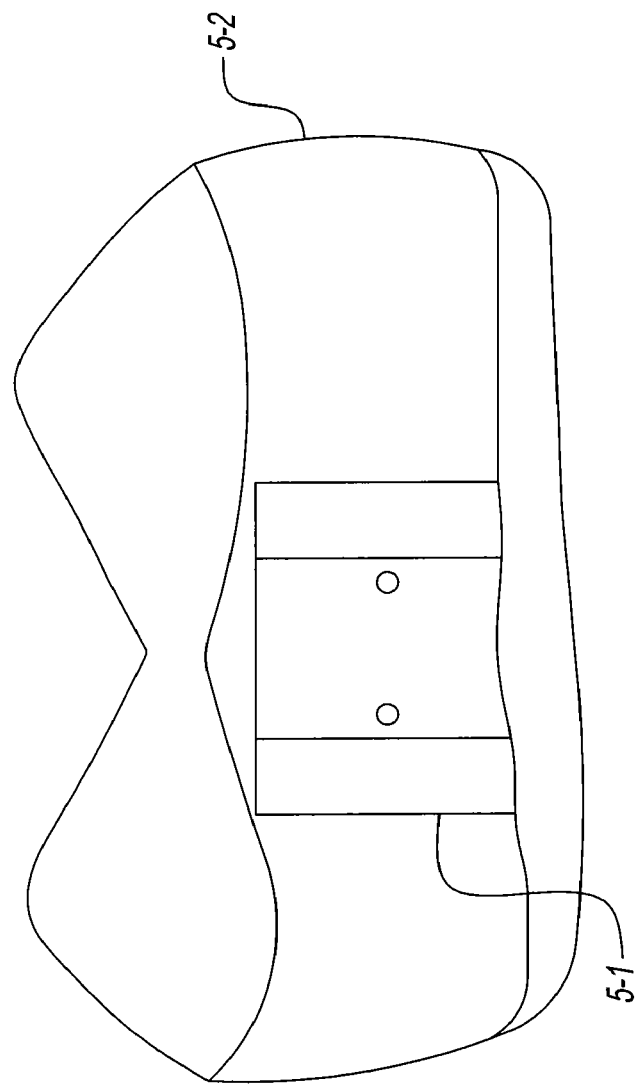

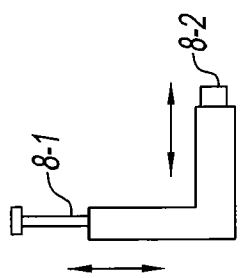
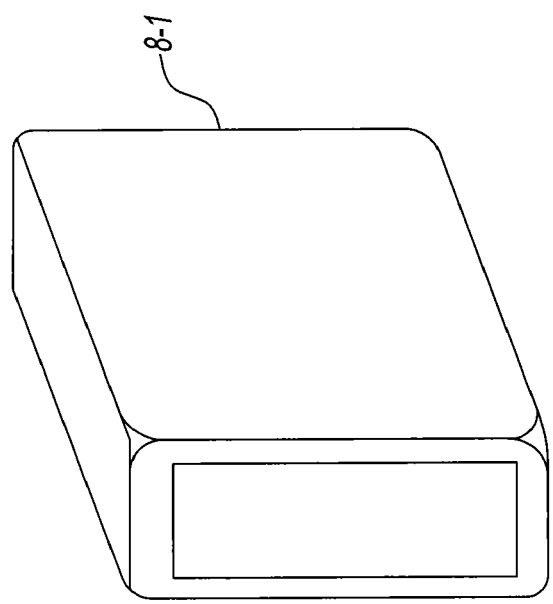

0
ORTHODONTIC DEVICE

GRANT OF NON-EXCLUSIVE RIGHT

This application was prepared with financial support from the Saudi Arabian Cultural Mission, and in consideration therefore the present inventor(s) has granted The Kingdom of Saudi Arabia a non-exclusive right to practice the present invention.

FIELD OF THE INVENTION

The present invention relates to orthodontic/orthognathic device for correcting and changing tooth placements and bone structure, and a method of using orthodontic/orthognathic device for tooth movement, correcting syndromic conditions that affect the face and jaws. The device can be controlled by computer to direct tooth and bone placement.

BACKGROUND OF THE INVENTION

In 1928 conventional edgewise-orthodontic appliance was introduced by Edward H. Angle, and is considered as the foundation for the numerous appliance systems commercially available today. Different adjustments have been added to the system such as direct bonded bracket, twin brackets, different dimensions, lingual applications, rotating wings, preadjusted bracket, etc., but the edgewise mounting concept has remained.

Conventional orthodontic appliances include brackets attached to the surface of the teeth and series of archwires with different strength and flexibility. The wires are changed and/or adjusted periodically to gradually align teeth using force transferred through flexible or rigid wires with preadjusted arch form. This form of adjustment means all teeth will move to follow the preadjusted arch form even if some teeth are in proper position. This uncontrolled system shows the lack of individualization to fit specific needs of each patient and solve each problem independently.

Crowding is a chief complaint that been presented to orthodontic clinic for resolution. Extraction is the conventional option to make space and eliminate crowding of teeth. A distalization appliance can be an excellent option to move the posterior teeth distally and create enough space especially with deep bite cases, but conventional distalization appliances suffer from difficulty and the lack of control which makes this kind of appliance incompletely effective.

Distraction osteogenesis is a procedure that has been conventionally used to change bone structure by, for example, lengthening bones using a device that functions to apply expansion or distancing force on a bone after the bone has been surgically separated. Conventional distraction osteogenesis devices are used conventionally to either reposition the maxillary or the mandibular bones for patients with facial syndromes that include severe maxillary or mandibular deficiency (Crouzon, Apert, etc.). Distraction osteogenetic devices are encumbered with difficulties relating to controlling the direction of movement and force applied to a bone and with cooperation of the patient who may be under distress or discomfort caused by the device.

An orthodontic palatal expander is an appliance that been used to expand constricted maxilla and conventionally includes bands attached to the posterior teeth. Such conventional devices have a screw in the middle of the palate that needs to be turned daily. A mandibular symphysis distraction device is used to expand severe constricted mandible.

Conventional orthodontic expanders and conventional distraction osteogenesis devices used for bone structure modification require periodic retensioning and adjustment in order to properly place teeth and/or modify bone structure in a desired manner. Such modifications usually require the intervention of an orthodontic, surgeon or other medical care professional at relatively great inconvenience and discomfort to the patient. Like orthodontic expanders, distraction osteogeneis devices often require daily maintenance and adjustment, e.g., by turning screws.

Technical literature describing contemporary tooth movement and bone biology research indicates that there are substantial variations in the results of clinical and animal studies. These variances arise for many reasons; one of the main reasons is the lack of a device and/or method that can produce accurate and reproducible force and tooth movement. The inconsistencies and low reproducibility of conventional devices can lead to inaccuracies during the experiments and difficulties in reproducing results. A computerized device that can be adjusted to provide specific force and type of movement could go a long way in alleviating such issues.

SUMMARY OF THE INVENTION

The present invention provides orthodontic and orthognathic devices that contains an electrically powered tensioning motor (electric motor) positioned and/or mounted inside or outside the mouth. The motor provides tension to teeth and/or bone structure through one or more lever arms that connect the tensioning motor of the orthodontic/orthognathic device to tooth or bone. The electric motor is encapsulated in a housing that is mounted to the palate or maxilla, or mandibular bones, and/or is anchored to posterior or anterior teeth, or mounted externally on the rigid frame of the distraction.

The orthodontic/orthognathic device is capable of exerting force on a tooth or bone structure in a predictable and stepwise fashion. By controlling the electric motor of the orthodontic device with a microcontroller that is included in the housing in which the electric motor is located permits customization of treatment plan and the application of force in a constant manner thus avoiding the necessity of several repeated visits to an orthodontic practitioner.

In one aspect of the invention the orthodontic device is attached to the palate, for example, with one or more mini screws. An electromotor powered by a battery (rechargeable) housed together or separately from the orthodontic device provides constant tension to a tooth through one or more lever arms that are connected to both the electromotor and a tooth. The electromotor may be programmed to provide tension to one or more teeth such that the teeth can be moved mesially, distally, buccally, labially, lingually, up or down direction with respect to the original tooth location. Any tooth may be connected to the electromotor and may be subject to tension or force through one or more lever arms. Orthodontic device can be an excellent treatment option for patient that has crowding and needs spaces to eliminate crowding with better and predictable result.

In another aspect of the invention the orthognathic device is used to correct conditions of the jaw and face related to the structure and the growth of skeletal bone and/or soft tissues of the face.

In a still further aspect of the invention computerized maxillary distraction is accomplished with the orthodontic and/or orthognathic device of the invention. Using electromotors positioned in a motor housing and programmed with instructions to move bones in particular direction in three dimensions permits facial changes and rearrangements both with functional, cosmetic and medical purposes. Computer control permits gentle and continuous exertion of force to improve patient comfort levels and reduce daily adjustment management. Maxillary movement can be programmed in three dimensions to accomplish advancement of maxilla but also to correct asymmetry or cant of the maxilla and/or change the morphology of bone and the growth patterns in cranial facial structures of a patient. Constricted and deficient maxilla can be expanded and advanced with a single orthognathic and/or orthodontic device. Conventionally such movement required two different devices and/or corrective appliances.

The device may also be used for osteogenic distraction for correcting skeletal deformities or injuries to the mouth. The orthognathic device may be used in a syndromic patient, often a younger individual suffering from skeletal deficiencies. The orthognathic device may be used to separate bone structure, for example to broaden or lengthening the mandible, or reposition other bones relative to one another in the maxilla.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 1 shows a base plate for the orthodontic device;
FIG. 4 shows a motor connected to one or more lever arms to a tooth mount;
FIG. 5 shows a lingual bracket;
FIG. 8A shows a motor housing containing components of an orthognathic device;
FIG. 8B shows lever arms for connecting to bone or tooth.

DETAILED DESCRIPTION OF THE INVENTION

Figure 3:
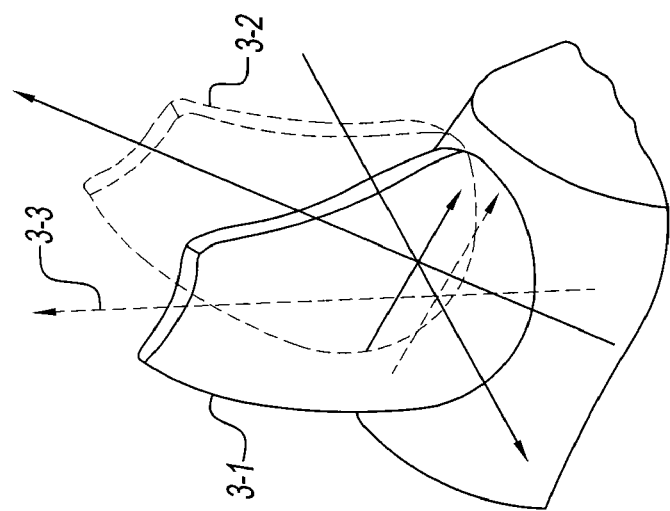
FIG. 3 shows angular movement of a tooth.

Conventional orthodontic devices or appliances are universal appliances that are applied to all patients with lack of individualization to fit specific need of each patient and solve each problem independently. Even such relatively simple movement is disadvantaged because it requires anchoring the orthodontic device, e.g., edgewise system, to other teeth. Thus the movement of a single tooth with a conventional orthodontic device may often result in movement of other teeth. This problem can be especially serious for patients having one or more teeth, which are unsuitable for anchorage and/or unsuitable for movement or contact with an orthodontic device.

Utilizing a motor mounted to the palate or other bone permits movement of single teeth in three dimensions. A tooth may be rotated, extruded/intruded, or labial/buccally, mesial/distally moved. A single tooth can be moved independently of other teeth or may be moved in conjunction with one or more teeth which are subject to pressure or tension from the motor of the orthodontic device. Not only can the orthodontic device move individual teeth separately, neighboring teeth may be subject to opposing forces. For example, a first tooth may be pushed outward and lifted whereas a neighboring tooth may be pulled inward and subjected to downward or lateral pressure. Connectivity with the bone structure such as the palate and/or mandible allows the orthodontic device to act on individual teeth without affecting neighboring teeth. The device can be mounted on the lingual or buccal surfaces of the mandible.

Tooth movement achieved by the device can be directed and/or programmed by using specially programmed computers and/or special purpose machines connected to a computer. The computer may include instructions to operably move teeth and/or bone according to a three dimensional map. Movement may be according to cephalometric analysis and/or norms used in the orthodontic field.

An important advantage of the orthodontic device resides in the ability to program constant force or tension on one or more teeth. Conventional devices which utilize tension means such as wires, spring, or screws require regular adjustment. Each adjustment places one or more teeth under an initial high strain which gradually dissipates as the tooth moves to accommodate force. The consequence to the patient is a period of heightened pain and discomfort immediately following the adjustment. Conventional orthodontic devices therefore subject the patient to periods of intense discomfort followed by a period of adjustment. In contrast, the orthodontic device described herein can be programmed to exert a constant force or tension thus avoiding the heightened and/or intense discomfort and pain which accompanies the periodic adjustments of conventional orthodontic devices. During the period of tensioning or adjustment in the orthodontic device a patient typically becomes accustomed to the tension or force and thus suffers substantially less discomfort than the periodic tensioning and adjustment in conventional orthodontic devices.

The same advantages apply for osteogenic distraction devices. Conventionally such devices require periodic tensioning and adjustment. Upon an increase in tension and separation of bones a patient may suffer severe pain and distress which only gradually dissipates after a period of hours or days. The exertion of a constant force or tension utilizing the orthodontic device avoids the intense period of pain associated with the adjustment in conventional osteogenic distraction devices.

The motor and associated housing of the orthodontic device may be mounted to bone structure in the mouth. Preferably, for orthodontic applications, the motor housing is attached to the palate of the mouth with, for example, a mini screw. The motor may be directly bonded to the palate but is preferably first mounted onto a plate (a palate plate) which may be of metallic or synthetic polymer construction.

A metal palate plate is preferred for improved hygiene for the patient. The motor housing may have an attachment means to the plate such that the motor housing can be repositioned and/or replaced with a new motor. The palate plate is optionally a polymeric synthetic material which can be molded to match the palate structure of the patient. The motor housing may be integrated into the polymeric material which is cured in place and/or cured on a mold made according to the shape of the patient's palate. Preferably the motor housing is removable to permit servicing and replacement when necessary.

The plate may cover a substantial portion of the palate or may be small so that less than 50%, preferably less than 25% of the aerial coverage of the palate is in contact with the plate or otherwise covered with the plate. A plate having a relatively small area is preferably attached by one or more mini screws to the palate. The plate may extend from the anterior portion distally across the entire palate to the posterior portion of the palate. The plate may rest in contact with the base of one or more teeth but preferably the base is independent and separated from any teeth.

The device may include a display screen or display indicator on which diagnostic information relating to the motor and/or the power source is displayed. The display screen or indicator is mounted together with the micromotor on the miniplate. The screen or indicator may be used to signal information such as whether sufficient power is available, whether the micromotor is activated, whether the device is "on" or "off" and/or positional information relating the movement of the bone or tooth.

In one embodiment the motor and motor housing are entirely encapsulated by the synthetic polymeric material which is in direct contact with the palate. In this configuration the electromotor is separated from and protected during mastication.

FIG. 1 shows a base plate (1) for the orthodontic device. In the embodiment shown in FIG. 1 the base plate is a single piece having a plurality of holes (3) for fitting a mini screw for attachment to the palate of a patient. The side of the plate facing inward to the mouth cavity includes a mounting bracket for the motor and motor housing. Shown in FIG. 1 is a mounting bracket in which a motor is held in place on two rails or connectors (2) that may be recessed or may protrude from the plate. The motor may be held in place by one or more additional fasteners which connect the motor housing to the base plate and restrict movement on the rails.

In other embodiments the plate includes a different number of holes or attachment points for mini screws. The mini screws are preferably located in a central portion between the mounting mechanism for the motor housing but may also or alternatively be located towards the wing sections or apex of the base plate shown in FIG. 1. For example, in one embodiment a mini screw is located at each of the rounded apexes (4) of the base plate. Likewise, instead of having rails as a mounting mechanism for the motor housing one or more protrusions may extend from the surface of the base plate facing inward to the mouth cavity for attachment. Such attachment means can be mechanical, e.g., by screw or chemical, e.g., by use of an adhesive.

In still a further embodiment the base plate is a synthetic polymer molded from a material such acrylic or preferably metal to match the surface contours of the palate. The surface facing inward to the mouth cavity may include an attachment location molded into the structure of the base plate. The attachment location may fit the motor housing and provide a socket in which the motor housing resides and is held in place either through a tension mechanism provided by the metal or acrylic base plate or by one or more additional retention means such as a screw or wire which may be molded into or fastened into the base plate.

In other embodiments of the invention the base plate includes more than one part. The base plate may have forward, rearward and/or side portions which may be connected to a main portion or other portions by a connecting means such as a metallic bridge. Such separate portions may be individually connected to the palate by an attachment means such as a mini screw or may alternately serve as a stabilization mechanism in a catamaran-type configuration.

A base plate that contains multiple portions allows a portion of the palate to remain exposed and free of the base plate. Thus the anterior or posterior portion of the palate may remain free or only partially covered with a base plate.

When constructed from a synthetic polymeric material the base plate is preferably made from an acrylic. The acrylic base plate may be molded directly onto the palate but is preferably formed separately and exterior of the palate using, for example, a mold formed from standard dental techniques. Metals are preferred over polymer plates to achieve improved hygiene in the mouth. Alternately the base plate may be used from an inert polymer such as a polyolefin with selection of the polyolefinic material based on preference for certain properties in the base plate such as stiffness, resistance to degradation, elasticity or transparency. Such polyolefinic polymers include polyethylene, polypropylene, ABS, polybutene, or polyvinylchloride. Other polymeric materials may be selected depending on the need for certain engineering properties such as break resistance, e.g., polycarbonate, polyamide and polyether sulfone.

Suitable metallic materials for the plate include stainless steel and alloys or other metallic elements. In one embodiment of the invention the plate is made of a corrosion resistant and inert metallic material such as titanium. Alloys of titanium and/or nickel may also be used to make the plate. Conventional metals and/or metallic alloys such as stainless steel, chromium cobalt, metallic denture materials and Nitinol used for dental applications are preferable.

The orthodontic device may function to distilize molars. Unlike conventional distilization procedures the orthodontic device may accomplish distilization without movement of any anterior teeth. Movement of the first, second or third molars distally is possible without movement of any bicuspid or incisor tooth. Movement of a single molar can also be accomplished without moving a second or third molar. Movement may be accomplished to retract, advance, extrude, intrude or rotate a molar independently of other teeth.

The orthodontic device may likewise function to move incisor or bicuspid teeth, either individually or in groups. Teeth may be moved in groups such that the teeth of the right and left side of the mouth are moved laterally in a spreading fashion. The orthodontic device provides an expanding linear force outwardly from the palate in a roughly equal amount to each side of the mouth. Expansion of the teeth may occur individually or in groups.

Movement of the teeth may also be along a lingual or buccal axis. In this manner a tooth having a top surface directed at an uneven angle either towards a buccal or lingual direction can be corrected such that the tooth sets in a proper axis to the mandible.

Figure 2:
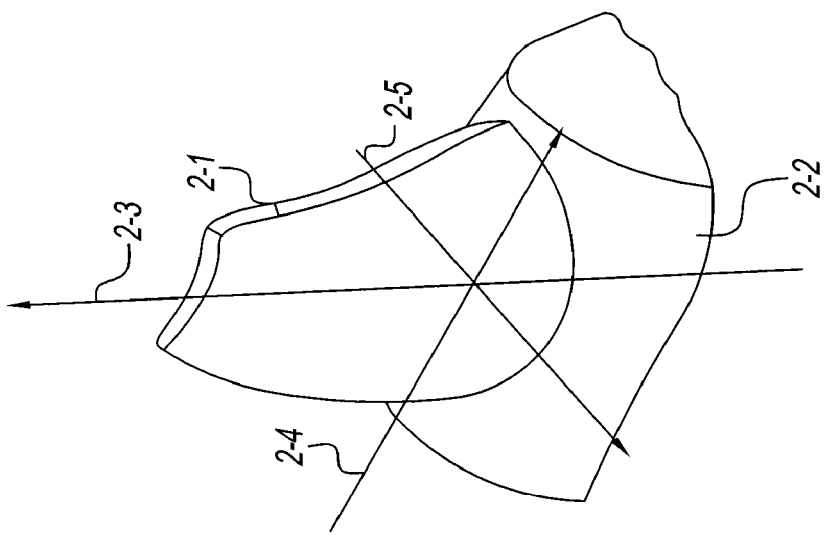
FIG. 2 shows a tooth embedded in a mandible or maxilla.

FIG. 2 shows a tooth (2-1) embedded in a gum line (2-2) of a patient's mandible or maxilla. The position of the tooth may be described according to the axes x (2-4), y (2-3) and z (2-5) which define three directions of movement for the tooth at a particular location on the mandible. The z axis generally defines the buccal-lingual movement, the x axis defines distal movement and the y axis defines lifting or depression of the tooth in the maxilla or mandible. The orthodontic device permits movement of a tooth along any of the axes x, y and/or z and likewise provides rotation around any axis r, p and q. For example, a tooth may be rotated around the axis y without otherwise being subject to movement in the x or z directions.

FIG. 3 shows angular movement of a tooth (3-1) together with movement in a buccal direction (3-2). The tooth is moved from a first position S to a second position S' that shifts the y axis in a buccal direction. Movement vertically in the y axis is shown by (3-3).

The motor which is used to generate pulling (tension) or pushing force on one or more teeth is preferably a micro motor. Examples of micro motors include piezo motors and electromagnetic motors. High torque rotary piezoelectric motors can be used and provide forces up to 5 N. Piezoelectric motors may be used in a step wide fashion providing screw speeds of, for example, from 1 µm/second to 10 mm/second. A high-torque rotary piezoelectric motor provides the advantage of programmable bursts of movement which are substantially undetectable by a patient. Commercially available piezoelectric motors from New Scale Technologies including the Squiggle® micro motor may be used in the motor of the orthodontic device. DC micro motors may also be used in the orthodontic device. A DC micro motor may be used in combination with one or more micro-planetary gears to provide force or tension to individual teeth. Brushless micro motors can be used the orthodontic device.

In an embodiment of the invention the motor and motor housing includes a removable and replaceable battery. When programmed to operate in a stepwise fashion battery life can be extended dramatically by periodic increases in force or tension which result in a substantially constant force or tension on a tooth. The battery may also be recharged through an external connection such as a micro-USB connection present in the motor housing.

A microprocessor controller is used in conjunction with the micro motor and is preferably housed together with the motor in the motor housing. The microprocessor controls forces exerted by the motor onto the teeth. The microprocessor may be pre-programmed with a force regiment or may be updated periodically with each update providing specific motor instructions for particular teeth. The microprocessor controls force and/or tension along any axis or direction with a force ranging from about 0.02 N to about 10 N depending on the micro motor and the tolerance threshold of the patient. The motor may be programmed by the microprocessor to provide either static or dynamic forces to a tooth. A static force operates by providing an initial force amount to a tooth followed by locking of the force. A dynamic force model includes constant adjustment of force through intermittent increases and/or decreases of force or tension from the motor conveyed to the teeth. Microprocessor control allows the force generated by the motor to be conveyed in the proper orientation controlling for any distortion or movement in the linkage.

The microprocessor is preferably programmed wirelessly. Any wireless connection may be used, preferably an electromagnetic connection by which instructions for motor movement are transferred onto a storage mechanism present with the micro motor in the housing provided on the plate of the orthodontic device. Instructions for force to provide specific rotation and angulation degrees for one or more teeth and/or one or more lever arms connected to teeth can be programmed into the orthodontic device. The motor housing may further include a battery, arduino board, bread board, resistors, sensors, transistor, LEDs, bluetooth mechanism in combination with one or more motors. The microprocessor may be one of the components of the arduino board and/or bread board. The device may be interconnected wirelessly to one or more electronic networks to provide and/or download instructions provided from a remote location.

The orthodontic device may be protected by a password and/or proprietary software restricting modification of instructions to the orthodontic device. Such protection enables the orthodontic device to remain under the control of a primary treating orthodontist or practitioner and encourages the patient to maintain a treatment regimen that is effective when complete. In one embodiment a patient may download motor instructions from the internet on a daily, weekly, or monthly basis depending on a treatment regimen provided by a treating practitioner. Motor instructions may first be downloaded to a wireless device which separately establishes contact with the microprocessor and motor of the orthodontic device. Information can likewise be loaded from the orthodontic device for analysis by a treating practitioner at a remote location. Such information may include information selected from one or more sensors present in the housing or present on one or more of the lever arms or lingual brackets. Based on information provided by the sensors the treating practitioner may modify or make changes to the instructions or force regimen provided by the orthodontic device to the patient's teeth. Operation from a remote location provides a degree of flexibility and efficiency that is not available with conventional orthodontic devices which may require mechanical adjustments on a periodic basis where such adjustments are made by a qualified practitioner.

FIG. 4 shows an embodiment of the invention wherein a motor (4-1) housed in a plate (4-2) is connected to one or more lever arms (4-4) to a tooth mount (4-3). The lever arms are preferably made of a metallic material that is resistive to bending and shows no distortion when conveying force from the motor of the orthodontic device to a tooth. In an aspect of the invention this connection is a "lever arm" which is directly attached to the motor or attached through a variable linkage. FIG. 4 shows a variable linkage (4-5). The linkage provides a connection from the lever arm to the motor.

The lever arm is connected to one or more teeth in a gate-type lingual bracket mounted on the inside surface of a tooth in a vertical or horizontal orientation. The lever arm may be connected to the lingual bracket in a permanent or temporary fashion. When permanently attached the lever arm is directly bonded to the lingual bracket. Preferably the lever arm terminates in a t-shape to connect with the lingual bracket in a manner which allows the lever arm to be separately disconnected from the lingual bracket. FIG. 4 shows a plate housing a motor having two linkages to lever arms. In other embodiments of the invention the motor is connected to a single lever arm or more than two lever arms. Likewise, a single lever arm may be connected to a single tooth through the gate-type lingual bracket or may be connected to a plurality of teeth through one or more gate-type brackets.

The lever arm is capable of exerting force on the teeth lingually or bucally. The micromotor thus moves the lever arm in three dimensions including left to right, rotationally, and up/down. The lever arm can be connected to the anterior or posterior teeth.

FIG. 5 shows a base of a lingual bracket (5-1) having a vertically oriented slot (5-2) on a tooth. The lingual bracket includes a gate for securing the lever arm to the tooth. The gate can be closed and fastened after insertion of the end of the lever arm. The lingual bracket may be attached to the inner surface of a tooth using conventional dental techniques and/or adhesives. It is preferable that the lingual bracket is bonded to only the interior/lingual surface of the tooth and is otherwise not exposed on the buccal side of the tooth. Cosmetic advantages are realized when the orthodontic device is out of sight and present only on interior surfaces of the teeth ordinarily not viewable during day-to-day human-human contact. The lingual bracket may extend under the gum line of the tooth or may terminate prior to the gum line. The lingual bracket may be connected with a vertical portion of the tooth representing from 100 to 10% of the vertically exposed surface of the lingual side of the tooth. In some embodiments the lingual bracket is narrow and covers only a small fraction of the lingual surface, e.g., 10-60, 20-40 or 30-40% of the lingual vertical surface of the tooth. More or less contact of the lingual bracket with the tooth may permit easier intrusion or extrusion of the tooth in buccal or lingual orientations and/or permit easier lift or depression of a tooth.

Figure 6:
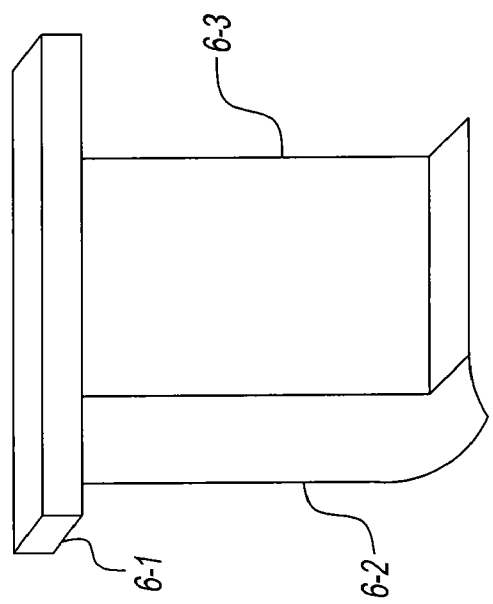
FIG. 6 shows a t-shaped terminus of a lever arm.

FIG. 6 describes the t-shaped terminus (6-3) of the lever arm connecting the micro motor of the orthodontic device with the lingual bracket attached to a tooth. The t-shaped terminus slides or is held into the slot provided by the lingual bracket and is the final connection between the lever arm and the tooth. The t-shaped terminus preferably rests inside the lingual bracket such that the terminus is unable to move loosely in the lingual bracket. The t-shaped terminus has a cap (6-1) connected to a body (6-2) that is fitted against a tooth surface.

Figure 7:
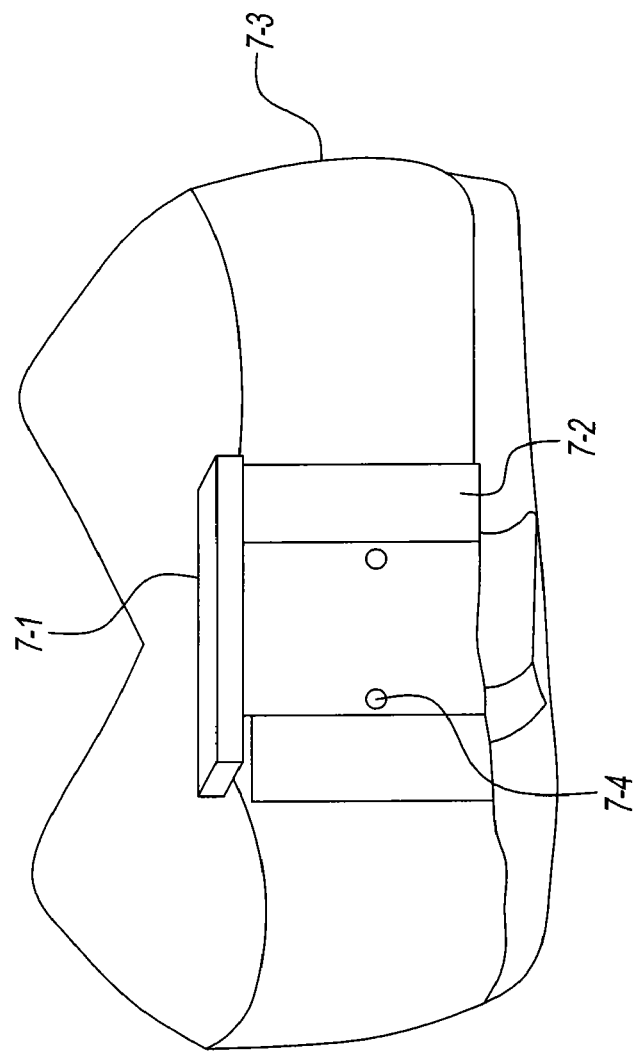
FIG. 7 shows a t-shaped terminus of a lever arm in a lingual bracket.

FIG. 7 shows the t-shaped terminus (7-1) in a lingual bracket (7-2) mounted to a tooth (7-3). The t-shaped terminus may be anchored to the lingual bracket through one or more screws or pin-type attachment means (7-4) to further ensure that there is no travel between the terminus of the lever arm and the lingual bracket and that the entire force exerted by the motor of the orthodontic device is transferred in the desired orientation to the tooth.

When used as a orthognathic device the motor and motor housing may be mounted on the palate in the mouth as described herein for the orthodontic device. Motors may be connected to bone structure such as the maxilla or zygomatic or mandible bone to permit movement and reorganization of facial structures and correct congenital conditions like cleft palate.

The orthognathic device may be directly connected to bones which require movement through a lever arm through, for example, mini screws. Upon undergoing orthognathic surgery such that bone structure is cut, the orthognathic device may be programmed to move bone slowly to permit reconstruction or rearrangement of facial and cranial facial features.

As an orthognathic device the motor may be present in a housing which is connected to one or more lever arms. FIG. 8A describes the motor housing (8-1) which may contain the motor, battery, Arduino board, breadboard, one or more resistors, one or more sensors, one or more transistors, one or more LEDs, and a nano Bluetooth shield. FIG. 8 describes the motor housing in rectangular block form. Other shapes may be used and are not limited to a block shape but include spherical shapes, cubic and cuboid shapes, cylindrical and hexagonal prismatic shapes, cone-shapes square-based and triangular-based pyramidic shapes and triangular prismatic shapes. Generally ovoid shapes are also useful. The lever arm is connected at one or more points to the motor through the motor housing. The lever arm functions to transmit forces from the electromotor to bone structure of a patient. For example the electromotor may exert forces on bones in the jaw or face through the lever arm which is connected thereto by one or more connection means such as a mini screw. Alternately the lever arm may be connected to one or more teeth.

The orthognathic device may be mounted inside the mouth, for example to bone structure such as the mandible and/or palate. FIG. 8B shows lever arms (8-1 and 8-2) that may be used to connect to bone or tooth and convey force thereto in different directions. Alternately the orthognathic device may be bonded to teeth through a spring-type mechanism. Maxillary distraction orthognathic device is mounted outside the mouth on a rigid frame that is separately attached to the bone structure of a patient.

Figure 9:
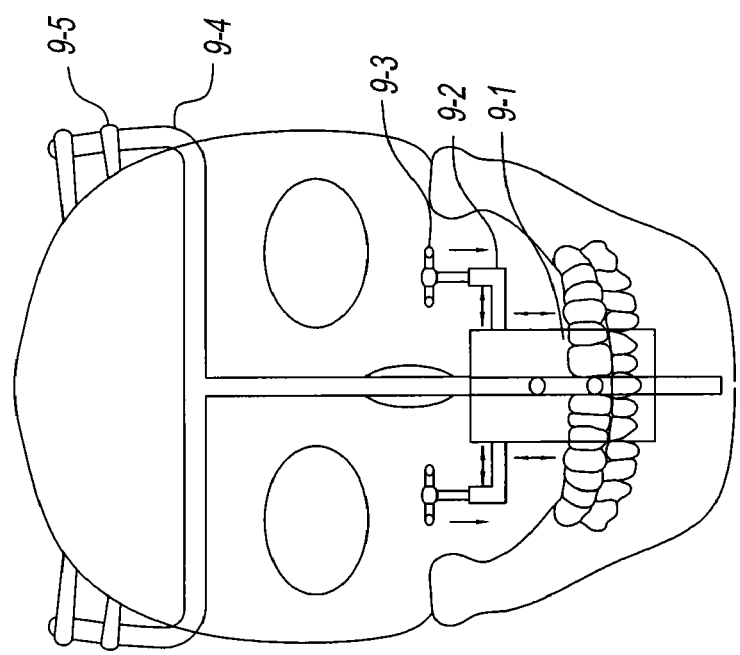
FIG. 9 shows an orthognathic device mounted externally on a rigid frame separately secured to bone structure of a patient.

FIG. 9 shows the motor and motor housing (9-1) connected to lever arms (9-2) which are able to exert force in different directions. The lever arms are separately connected to bone structure (9-3) and one or more teeth. The motor housing is mounted on a rigid frame (9-4) which is separately connected to the bone structure of the skull of a patient (9-5). In the embodiment shown in FIG. 9 the rigid frame has a "Y" type configuration permitting fixation to both sides of a patient's skull. When mounted exteriorly the orthognathic device may be in contact with one or more teeth either for stability purposes or for the purpose of exerting force and functioning to move and/or reposition teeth on the jaw. Preferably the rigid frame has at least three points of contact to bone structure of a patient. Such three points are demonstrated in FIG. 9 by two points at which the frame is attached to the skull with two screws and a third point at which the frame and/or motor housing is connected to the jaw and/or tooth structure permanently, semi permanently. In FIG. 9 the motor exerts force on the maxilla which permits movement and reconstruction or rearrangement of facial features.

Figure 10:
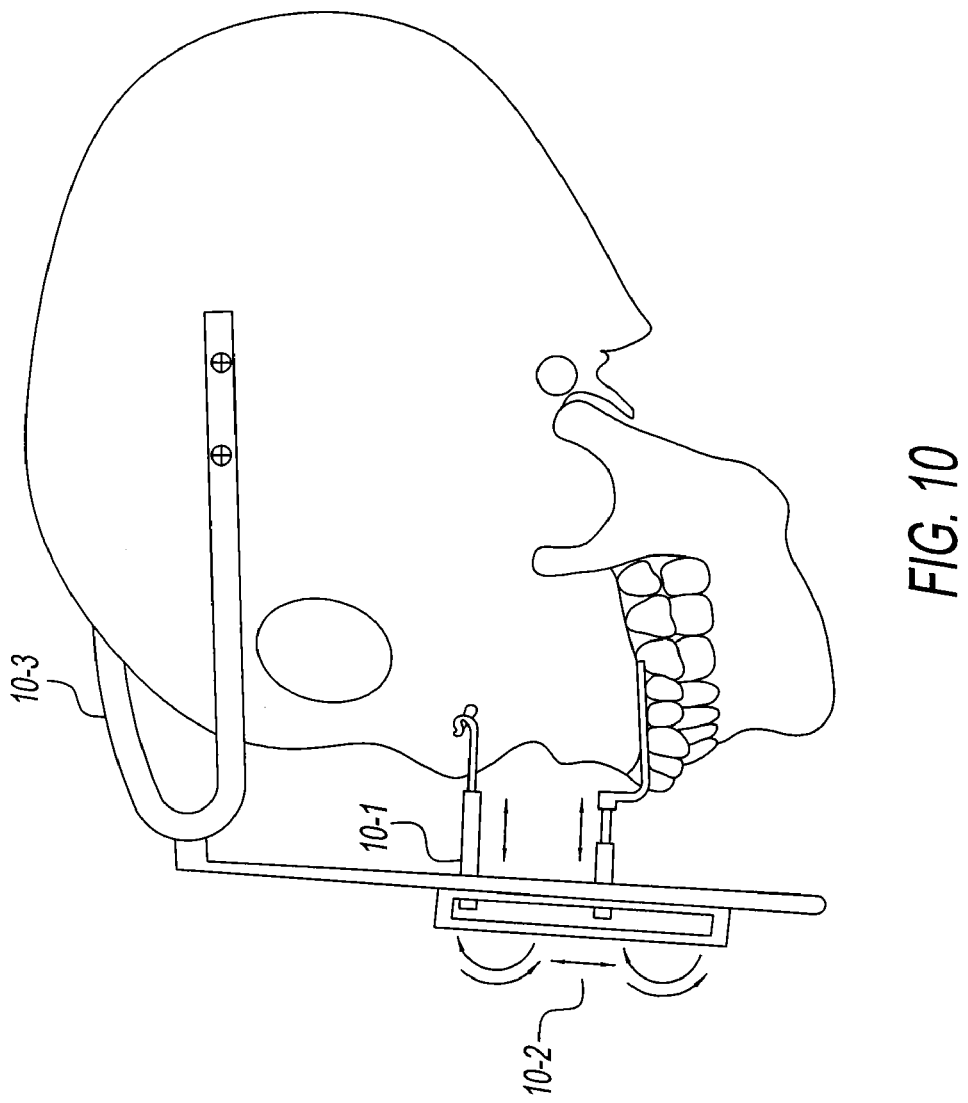
FIG. 10 shows a sagittal view of the orthognathic device.

FIG. 10 describes a side or sagittal view of the orthognathic device. Lever arms (10-1) connect the motor and motor housing (10-2) to both bone structure, maxilla, and to teeth. The motor may be programmed such that each lever arm moves independently to have a separate and distinct effect on bone and/or tooth movement. The motor and housing are mounted on a rigid frame (10-3).

In another embodiment of the invention the orthognathic device is used for osteogenetic modification or adjustments of a patient. Such adjustments include changes to craniofacial bone structure such as modification of mandibular structure. Other bones in the maxilla may likewise be influenced and corrected to change growth and development of craniofacial features. In a preferred embodiment the osteogenetic functionality of the orthodontic device is used to correct syndromic defects or deformities of a younger patient. Such changes are generally viewed as more efficient in a younger patient where bone structure has not yet fully hardened and sutures are separated and provide greater flexibility of movement.

Osteogenetic corrections preferably affect the bone structure of the patient but may also have an effect on soft tissues or tissue spaces of the patient. The advantages of the orthodontic/orthognathic device as they apply for correction of dental misalignment are likewise functional and useful for the orthodontic/orthognathic device in its use for correcting osteogenetic defects and/or deformities. Placement of the orthodontic device inside an oral cavity avoids external placement of conventional devices which are so placed in order for a physician or treating practitioner to make adjustments.

Some examples of osteogenetic defects and/or deformities that may be corrected with the orthodontic/orthognathic device include facial underdevelopment such as facial asymmetry or deficiencies, temporo-mandibular joint dysfunction, sleep apnea obstructions and, for example narrow chin in which the mandibles are too closely oriented at the apex.

Microprocessor control permits application of force onto bones or bone structure in three dimensions such that bones may be readjusted to correct for defects, damage or abnormalities. In this manner force may be applied statically or dynamically and is so-programmed by the microprocessor of the orthodontic device.

Figure 11:
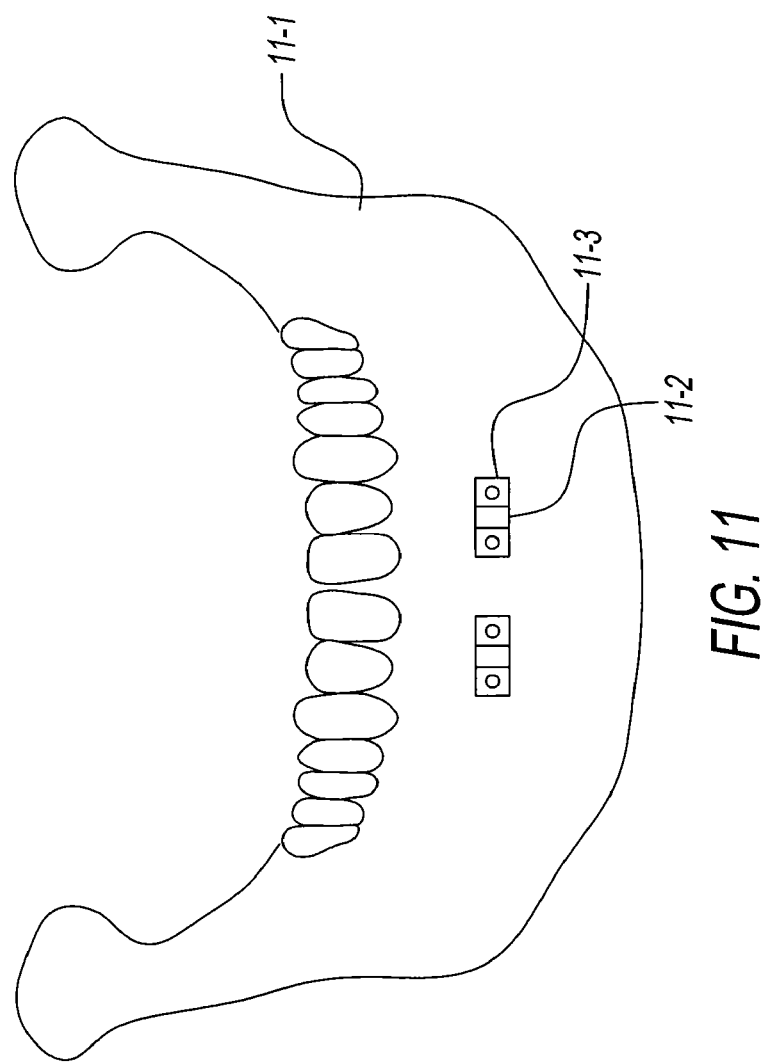
FIG. 11 describes a mandibular symphysis distraction device mounting scheme.

Particular defects that may be addressed include syndromic narrow mandible which can be addressed by an expansion rate of up to 1 mm/day using the orthodontic/orthognathic device of the invention on a younger or adult patient. In this aspect two micromotors are placed in two different housing and connected to each other with for example a sliding arm, and attached to the surgically separated mandiblular symphysis with miniplate. Each side of the mandible (11-1) is attached to a miniplate (11-2) held to bone by one or more miniscrews (11-3). The miniplates serve as a mounting position and anchorage for a micromotor (see FIG. 11).

A lateral expansion force is applied to symmetrically expand the mandible and provide the patient with relief for a narrow jaw. Other osteogenetic problems include constricted maxilla which can be addressed by palatal expansion using the orthodontic device. In this aspect the orthodontic device is locally anchored to the palate and connected to the teeth with lever arms serving and connecting different portions anteriorly and posteriorly. If the purpose of the expansion is only to tip the teeth buccally and not skeletal expansion, then expander can be only attached to the teeth without palatal anchorage. The same can be applied to constricted mandible.

Subsequent to complete dental readjustment and/or osteogenetic readjustment the orthodontic/orthognathic device is removed from the patient together with removal of micro screws used to anchor the device plate to the palate, mandible or facial bones of the patient.

Figure 12:
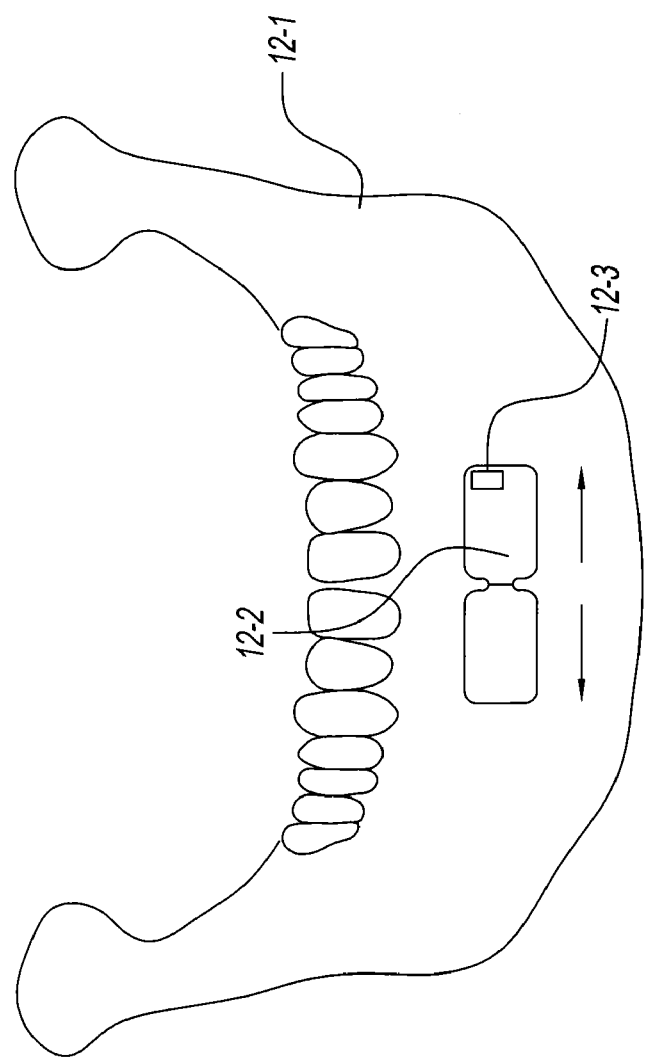
FIG. 12 shows a mandibular distraction device including motor for separating a mandible.

A micromotor mounted onto a mandible, interiorly or exteriorly, functions to apply a separating force to divide the mandible at a surgical separation. Distraction includes separating the sides of the mandible in a predetermined and preprogrammed manner. FIG. 12 shows a mandible (12-1) on which one or more micromotors (12-2) is mounted. Diagnostic information relating to the motor and/or the power source is displayed on a screen (12-3) that is mounted together with the micromotor on the miniplate. The screen may be used to signal information such as whether sufficient power is available, whether the micromotor is activated, whether the device is "on" or "off" and/or positional information relating the movement of the bone. indicates whether A single micromotor may be mounted and anchored to both miniplates or two separate micromotors connected to one another or separately connected to an opposite miniplate may be used. Preferably a micromotor is located between the miniplates and functions to distract the side of the mandible through an expanding force. The micromotor may be programmed to apply force in three dimensions to correct asymmetries of the mandible and/or to move each side of the mandible independently of the other side of the mandible. The micromotor is housed in a housing which can contain the same features, functions and components of the orthodontic and orthognathic devices described herein.

Figure 13:
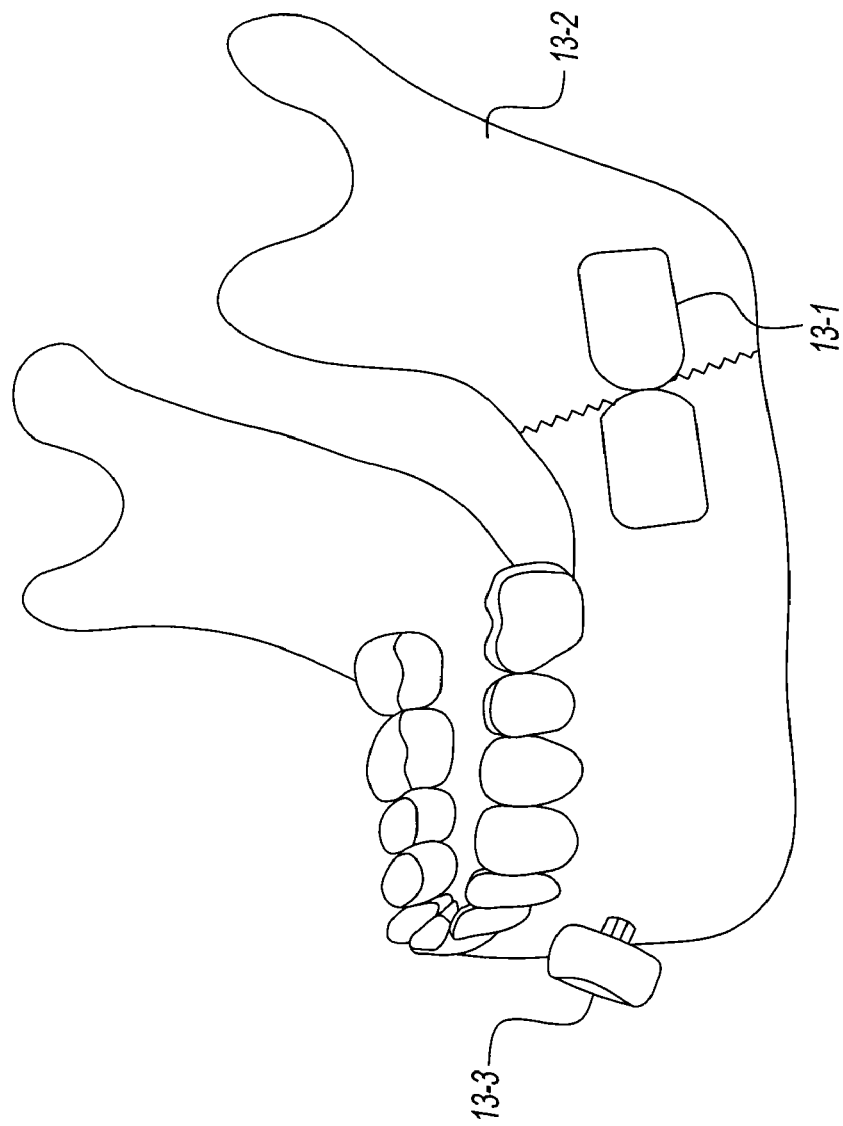
FIG. 13 shows a mandibular distraction device mounted on a side portion of a jaw for mandibular advancement.

The mandibular distraction device (13-1) may also be mounted to the side of a jaw (13-2) to perform lengthening osteogenetic distraction of a mandible. When mounted on the side at least miniplates are used to span surgical separation of the mandible (see the sagittal view of FIG. 13). Side-mounted micromotors may be used in conjunction to symphysis-mounted micromotors so that both mandibular advancement and mandibular midline distraction may occur simultaneously and/or concurrently. Like symphysis-mounted micromotor (13-3) the side-mounted motor may move each portion of the mandible independently in three dimensions to correct asymmetries.

In another aspect of the invention a palate-mounted micromotor is used as a maxillary palatal expander device. This embodiment of the invention is especially preferred for treating constricted maxilla. The palatal expander device may be preferably attached to a palatal surface in the roof of the mouth or, preferably, may be attached to a palatal surface of the teeth inside the mouth. The device may be present in one or more housings which contain, independently, a micromotor, microprocessor and other components such as those described herein for the orthodontic and/or orthognathic device (see FIGS. 14 and 15).

Figure 14:
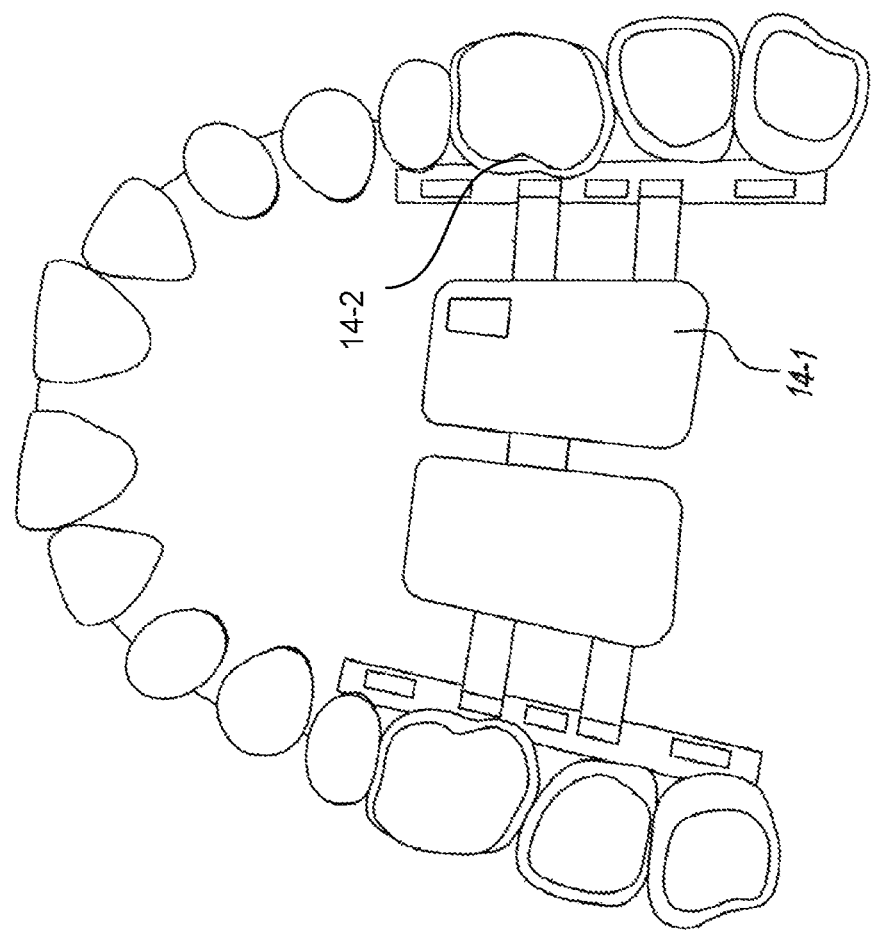
FIG. 14 shows a maxillary palatal expander device including a micromotor with attachment to the palatal and/or lingual surface of the tooth.
Figure 15:
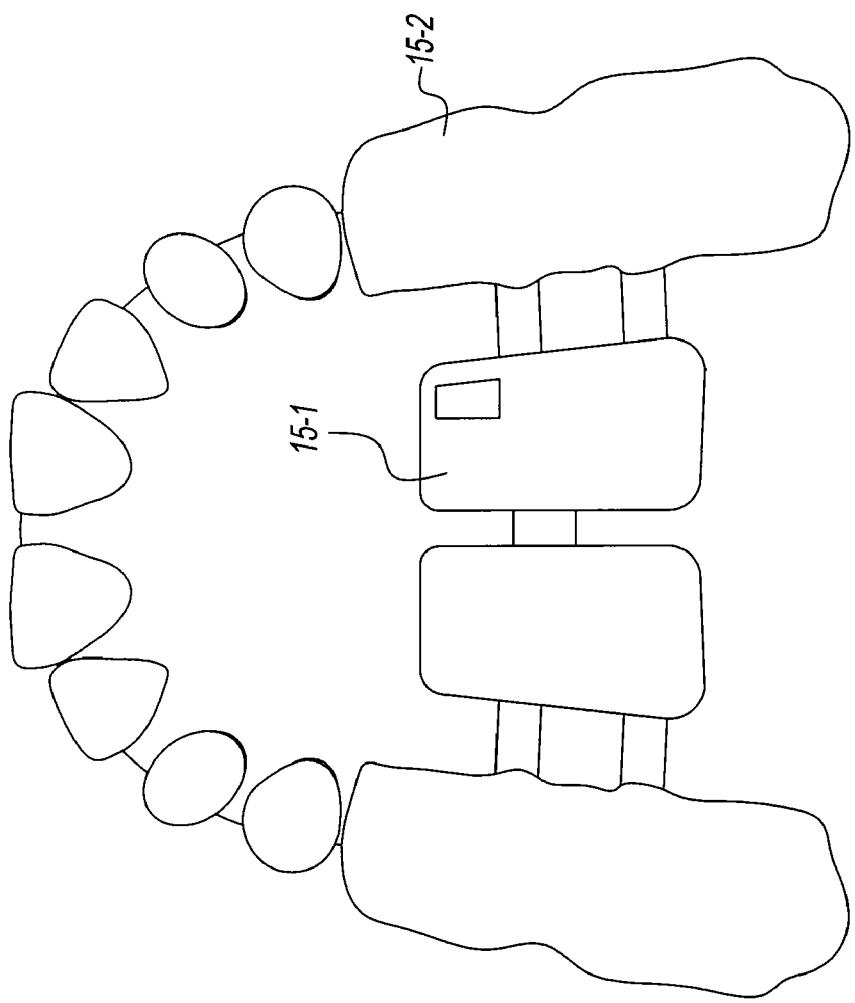
FIG. 15 shows a maxillary palatal expander device connected to teeth to the occlusal and palatal surface of the tooth through an acrylic adhesive.

In FIG. 14 the micromotors and housings (14-1) are located between gum lines and exert force directly on teeth (14-2). In FIG. 15 the micromotors and housings (15-1) are locate between gum lines and are connected to teeth through an adhesive tooth coating (15-2).

The use of motors in the maxillary palatal expander device is especially preferred for achieving buccal movement of the teeth. The sides of the mouth as expressed in the maxilla may be moved sidewards or inwardly. Either side may be moved independently and in three directions to correct asymmetries.

In an especially preferred embodiment of the invention the maxillary palatal expander device is mounted in the mouth through an acrylic adhesive connecting the micromotors and lever arms directly to one or more teeth and/or palatal surfaces of the teeth. The acrylic adhesive does not interrupt any tensioning or force exerted by the micromotors from the motor housing onto to the buccal teeth surfaces or palate, as needed (see FIG. 15).

Figure 16:
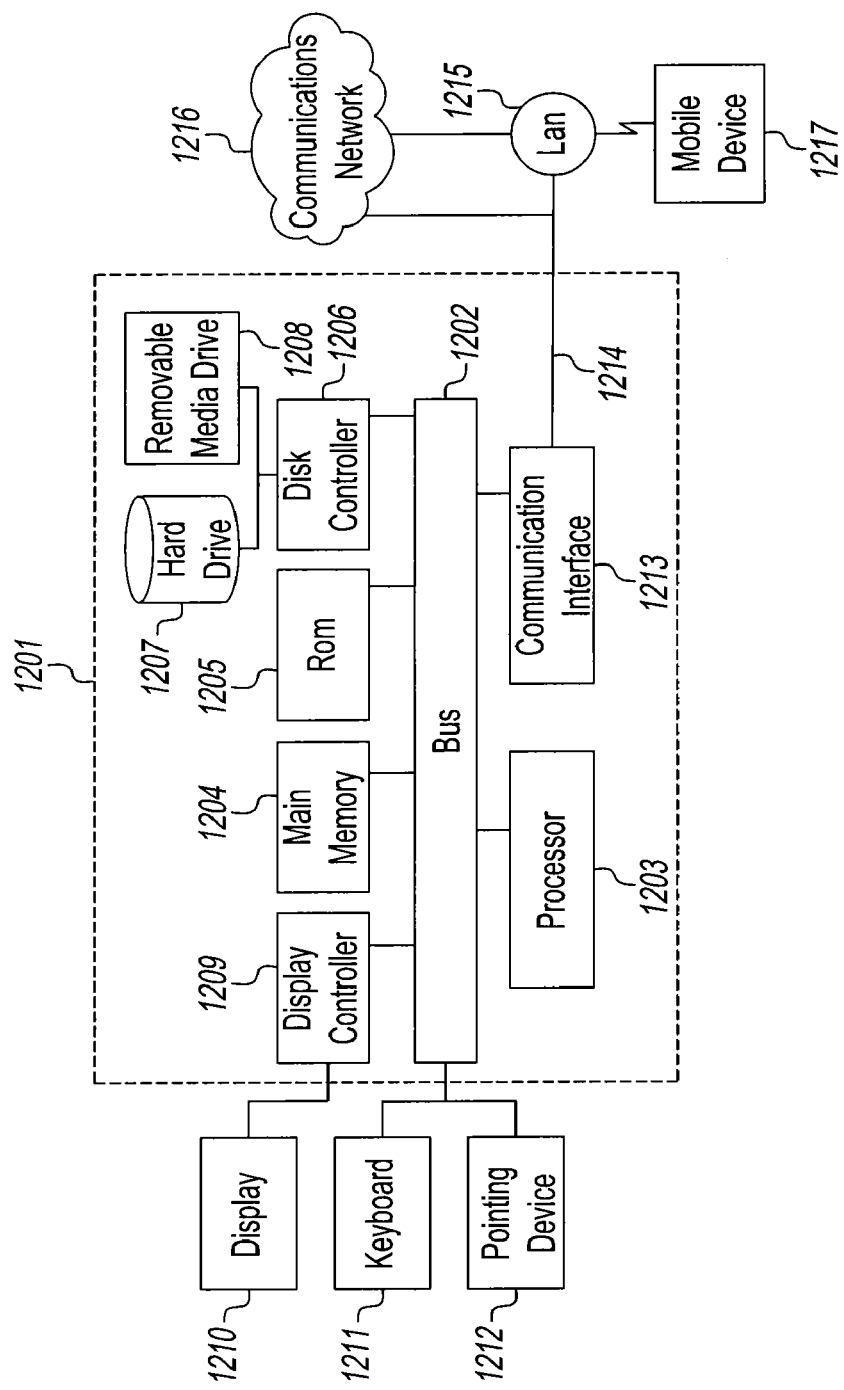
FIG. 16 shows computer equipment for controlling and/or communicating with the orthodontic device.

The orthodontic/orthognathic device may be connected to a computer device, wirelessly or through a hard connection. The computer device and/or orthodontic device may be constructed or have functionality as described herein. A hardware description of the computer device and/or orthodontic device according to exemplary embodiments is described with reference to FIG. 16. In FIG. 16, shows a CPU 1200 which performs processes for controlling the orthodontic device and/or for obtaining and analyzing information obtained from the orthodontic device. Process data (e.g., motor instructions and force measurements) and instructions may be stored in memory 1202. These processes and instructions may also be stored on a storage medium disk 1204 such as a hard drive (HDD) or portable storage medium or may be stored remotely. Further, the computer and microprocessor are not limited by the form of the computer-readable media on which the instructions of the inventive process and device are stored. For example, the instructions may be stored on CDs, DVDs, in FLASH memory, RAM, ROM, PROM, EPROM, EEPROM, hard disk or any other information processing device with which the orthodontic communicates, such as a server or computer.

Further, the claimed orthodontic/orthognathic device instructions may be provided as a utility application, background daemon, or component of an operating system, or combination thereof, executing in conjunction with CPU 1200 and an operating system such as Microsoft Windows 7, UNIX, Solaris, LINUX, Apple MAC-OS and other systems known to those skilled in the art.

CPU 1200 may be a Xenon or Core processor from Intel of America or an Opteron processor from AMD of America, or may be other processor types that would be recognized by one of ordinary skill in the art. Alternatively, the CPU 1200 may be implemented on an FPGA, ASIC, PLD or using discrete logic circuits, as one of ordinary skill in the art would recognize. Further, CPU 1200 may be implemented as multiple processors cooperatively working in parallel to perform the instructions of the inventive processes described above.

The computer architecture in FIG. 16 also includes a network controller 1206, such as an Intel Ethernet PRO network interface card from Intel Corporation of America, for interfacing with network 1212. As can be appreciated, the network 1212 can be a public network, such as the Internet, or a private network such as an LAN or WAN network, or any combination thereof and can also include PSTN or ISDN sub-networks. The network 1212 can also be wired, such as an Ethernet network, or can be wireless such as a cellular network including EDGE, 3G and 4G wireless cellular systems. The wireless network can also be WiFi, Bluetooth, or any other wireless form of communication that is known.

The computer architecture and supporting equipment may further includes a display controller 1208, such as a NVIDIA GeForce GTX or Quadro graphics adaptor from NVIDIA Corporation of America for interfacing with display 1210, such as a Hewlett Packard HPL2445w LCD monitor. A general purpose I/O interface 1212 interfaces with a keyboard and/or mouse 1214 as well as a touch screen panel 1216 on or separate from display 1210. General purpose I/O interface also connects to a variety of peripherals 1218 including printers and scanners, such as an OfficeJet or DeskJet from Hewlett Packard.

A general purpose storage controller 1224 connects the storage medium disk 1204 with communication bus 1226, which may be an ISA, EISA, VESA, PCI, or similar, for interconnecting all of the components. A description of the general features and functionality of the display 1210, keyboard and/or mouse 1214, as well as the display controller 1208, storage controller 1224, network controller 1206, sound controller 1220, and general purpose I/O interface 1212 is omitted herein for brevity as these features are known.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The invention claimed is:

1. A computerized orthodontic treatment device, comprising:
    a plate configured to mount to a palate of a patient through miniscrews;
    a micro motor and microprocessor present in a housing having mounting brackets that slide into a pair of rails of the plate;
    a lever arm connected to the micro motor through a linkage; and
    one or more lingual brackets connecting the lever arm to one or more teeth,
        wherein the lever arm is substantially resistant to deformation under force applied from the micro motor to a tooth and terminates in a T-shape to connect with the lingual bracket,
    wherein the micro motor is configured to move the lever arm three-dimensionally along a first direction, along a second direction substantially perpendicular to the first direction, and along a third direction substantially perpendicular to the first direction and the second direction, and
    wherein the micro motor and the microprocessor are connected to the plate and the micro motor is wirelessly programmable and contains operable instructions to apply force from the micro motor to one or more teeth.

2. The device of claim 1, wherein the orthodontic device does not have any arch wire.

3. The device of claim 1, wherein the micro motor is connected with a lingual surface or a buccal surface of a tooth.

4. The device of claim 1, wherein the plate is being molded to match a curved surface of the palate and rest in contact with a base of one or more teeth.

5. The device of claim 4, wherein the curved surface covers an entirety of the palate.

6. The device of claim 5, wherein the plate is made of a molded polymeric synthetic material.

7. The device of claim 1, wherein the miniscrews are located at rounded apexes of the plate.

8. The device of claim 1, wherein the plate further includes an additional fastener to connect the housing to the plate and restrict movement of the housing along the pair of rails.

9. The device of claim 1, wherein the plate further includes a main portion affixed to the palate, and peripheral portions spaced apart from the main portion to leave between the main portion and the peripheral portions the palate exposed.

10. The device of claim 9, wherein the peripheral portions are affixed to the main portion through metallic bridges.

11. The device of claim 1, wherein the micro motor further includes a screen mounted on the plate to display diagnostic information.

12. The device of claim 11, wherein diagnostic information includes positional information relating to the teeth.

* * * * *